United States Patent [19]

Rosenberg

[11] 4,307,082
[45] Dec. 22, 1981

[54] METHOD FOR THE EXTRACTION OF A FACTOR THAT MEDIATES CONTACT INHIBITION OF CELL GROWTH

[75] Inventor: Martin J. Rosenberg, Brooklyn, N.Y.

[73] Assignee: New York University, New York, N.Y.

[21] Appl. No.: 56,393

[22] Filed: Jul. 10, 1979

[51] Int. Cl.³ .................. A61K 35/00; C12P 1/00
[52] U.S. Cl. ............................... 424/115; 424/123; 435/41; 435/240; 435/68; 435/948
[58] Field of Search .................. 435/68, 240, 41; 424/123, 124, 115

[56] References Cited

PUBLICATIONS

Lipkin et al., Proc. Nat. Acad. Sci. USA, vol. 71, No. 3, pp. 849-853 (1974).
Lipkin, Journal of Investigative Dermatology, vol. 57, pp. 49-65 (1971).
Lipkin et al., Cancer Research 38, pp. 635-643 (Mar. 1978).
Lipkin et al., Annals of the New York Academy of Sciences, vol. 312, pp. 382-391 (Jun. 20, 1978).

Primary Examiner—Alvin E. Tanenholtz
Attorney, Agent, or Firm—Darby & Darby

[57] ABSTRACT

Described herein is a method for the extraction of an active biochemical factor that restores contact inhibition of growth to malignant cell types of different mammalian species.

20 Claims, 1 Drawing Figure

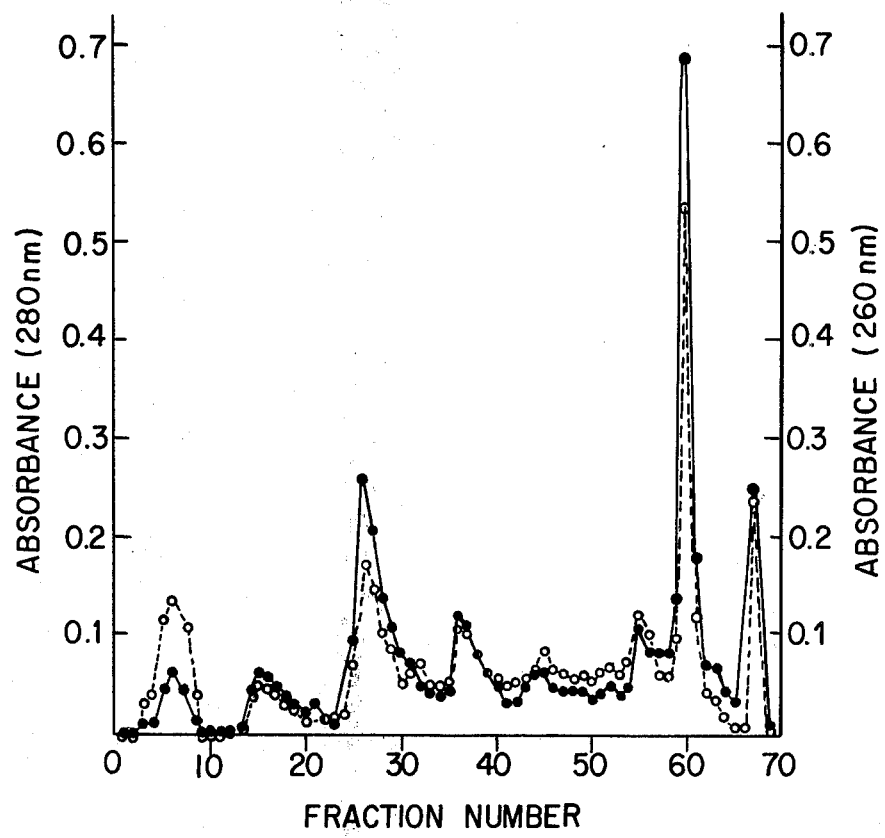

METHOD FOR THE EXTRACTION OF A FACTOR THAT MEDIATES CONTACT INHIBITION OF CELL GROWTH

The Government has rights in this invention pursuant to contract no. 5-T32-AMO-7190 awarded by the Department of Health, Education and Welfare.

This invention pertains to a method for the extraction of a contact inhibitory factor from a culture medium of contact inhibited cells. The factor has the ability to restore contact inhibition of growth to non-contact inhibited (malignant) cells.

Normal cells in vitro will characteristically exhibit a form of growth control termed "contact inhibition of growth", "density dependent inhibition of growth," of "topoinhibition". These terms refer to a cellular interaction dependent on population density and by which the growth of such normal cells is limited. When subconfluent cell cultures of these normal cells grow together to form confluent monolayers, their proliferation is halted. This occurs despite the fact that the culture medium in which the normal cells exist is still capable of supporting growth at lower cell densities. Saturation density is the term used to describe the population level at which the growth of such cells is arrested under predetermined culture conditions.

In contrast, it has been found that malignant cells do not exhibit this type of growth control; rather on reaching confluence under identical culture and growth conditions such cells will continue to multiply and form multilayered, disoriented cell groups. These malignant cell groups have significantly higher saturation densities than identical cultures of their being counterparts. A crude biochemical factor isolated from culture medium of a contact inhibited cell line has previously been identified and found to be capable of restoring the capacity for contact inhibition of growth to malignant cells of mammalian species. This factor has been termed contact inhibitory factor (or CIF).

In the past, a crude contact inhibitory factor has been isolated from biologically active fractions obtained from 48 to 72 hour old, serum-free conditioned culture medium of a contact inhibited hamster amelanotic malanoma cell line. Heretofore, the active fraction has been separated from the serum free conditioned media by molecular sieving on a Sephadex G-200 (Pharmacia Fine Chemicals AB, Piscataway, N.J.) column. The crude material obtained by this separatory technique from cultures of a contact inhibited melanocyte cell line, is capable of reversibly inducing in highly malignant melanocytes the capacity for contact inhibition of growth. The prior technique for separation of a crude contact inhibitory fraction is reported in an article in the Proceedings of the National Academy of Science, U.S.A. Vol. 71, Number 3, pages 849–853, March 1974 by Lipkin et al. Based upon protein content, the crude factor isolated by Lipkin et al had a specific activity of about 50 micrograms per milliliter and exhibited a pattern of multiple proteins on reduced SDS-polyacrylamide gels. Based upon the existence of multiple protein bands on polyacrylamide gels, it was recognized that the crude factor was relatively impure.

It has now been unexpectedly discovered that a further separation, yielding a more highly purified product, can be effected by hydrophobic interaction. In this technique substances are separated on the basis of the differing strengths of their hydrophobic interactions with an uncharged bed material which contains hydrophobic groups. The purified contact inhibitory fraction separated with this technique exhibits a substantially enhanced specific activity (at concentrations on the order of five micrograms per milliliter). This is a tenfold increase in activity as contrasted with the crude factor separated by the earlier molecular sieving procedure. As demonstrated on reduced SDS-polyacrylamide gels, the purified CIF material of the present invention contains a single, relatively narrow, protein band. This tends to confirm that the CIF of this invention contains many fewer proteins than the CIF isolated by means of molecular sieving, and is therefore a considerably purer product.

The present invention is based on the use of materials whose hydrophobic bonding interaction with proteins and other substances can be modified in the presence of buffers of varying ionic strength. One such material is phenyl-sepharose, a non-ionic hydrophobic affinity gel. In the presence of high ionic strength buffers phenyl-sepharose provides enhanced bonding interaction between the phenyl groups on the fractionation column and the hydrophobic moieties of proteins and other substances flowing through the column. Phenyl-sepharose is prepared by cross-linking agarose with 2, 3 dibromopropanol (British Pat. No. 1,352,613) and desulphating the resulting gel by alkaline hydrolysis under reducing conditions. Phenol groups are introduced into the gel matrix by reacting the gel matrix with the corresponding glycidyl ether. This reaction provides derivatives in which the phenol groups are attached to the monosaccharide units of the agarose matrix via uncharged, chemically stable ether linkages. The properties of this material are such that, in the presence of high ionic strength buffers, there is an enhancement of bonding interaction between the phenol constituents of the gel matrix and the hydrophobic region of a sample (e.g. a protein) in the vicinity of the gel. Hydrophobic proteins and other substances will bind to the column under high ionic strength conditions, permitting more hydrophilic materials (e.g. nucleic acids) to pass directly through. In the present invention the bound proteins are eluted according to increasing hydrophobicity by a stepwise decrease in the ionic strength of the eluting buffer followed by elution of the active (CIF containing) fraction with unbuffered distilled water. Other hydrophobic affinity gels suitable for use in the present invention include, for example, Octyl-Sepharose, Sephadex LH20 and Sephadex LH60. (Octyl-Sepharose, Sephadex LH20 and Sephadex LH60 are trademarks of Pharmacia Fine Chemicals AB, Piscataway, N.J.).

A contact inhibited cell line has been used to produce the protein containing extract capable of restoring contact inhibition of cell division. The contact inhibited cell line that will be used to illustrate the present invention arose during pigment transformation of a highly malignant, hamster amelanotic malignant melanoma cell line (Roswell Park Memorial Institute Number 1846) by nucleic acids derived from 7, 12-dimethylbenzene(a)anthracene (DMBA) induced, benign, highly pigmented, blue nevi of Syrian hamsters. In practice, highly pigmented benign blue nevi tumors are induced in Syrian hamsters by topical application of a single dose of DMBA. The benign tumor corresponds histologically to cellular blue nevi of humans. To obtain nucleic acids for incubations, 100 10–12-week-old female Syrian hamsters were painted with 1% DMBA and observed for 8–12 months until maximum blue nevus formation occurred in each animal. At such times, all palpable nevi were carefully excised, trimmed of overlying skin and underlying subcutaneous fat, and frozen at −70° C. until ready for use. When sufficient material had been collected, the frozen, pooled nevi were used as a source of nucleic acids, the latter being extracted with the phenol method. Because of the small quantities of material available, the pooled RNA and DNA obtained was not further separated but used as a mixture in the ratio of 10:1 (RNA:DNA) in incubations. Prior to use the pooled nucleic acids were stored for up to 6 months at −20° C. The purity and concentrations of RNA and DNA were determined by employing UV spectroscopy, and oricinol and indole measurements. Using conventional tissue culture and extraction procedures, the pooled nucleic acids from the benign melanotic (pigmented) nevi cells were added to tissue cultures of amelanotic (RPMI No. 1846) malignant melanoma cells. As a result of this operation, a new cell line (maintained as ATCC No. CRL-1479) was derived from the hamster amelanotic malignant melanoma line (RPMI No. 1846). The transformation technique is described in more detail in an article by Lipkin in Journal of Investigative Dermatology Vol. 57, pp. 49–65 (1971). The new cell line contains both pigmented and amelanotic cells with stable, hereditary properties that differ from those of the parental malignant (RPMI 1846) precursor line. The pigmented (melanotic) transformants proliferated at a much reduced rate, equivalent to about 20% of the poliferation rate of the parent cell line and are of no interest in this invention. Although aneuploid, the amelanotic (non-pigmented) transformants had the property of density dependent inhibition of cell division and showed such features of increased contact inhibition as growth in monolayers of parallel oriented cells, decreased maximum plate density and increased adherence to the culture plate. Cytophotometric examination showed that the new cell line (ATCC No. CRL-1479) had a hypertetraploid complement of DNA, in contrast to the hyperoctaploid content of the parent cells. In vivo transplantation of the new cells gave a significant delay in appearance of malignant tumors, with prolonged survival of recipients. The new cell line is available from the American Type Culutre Collection as ATCC No. CRL-1479.

To obtain starting materials for the practice of the present invention, cultures of the new contact inhibited cell line (ATCC No. CRL-1479) were maintained in Falcon T-60 plastic flasks (No. 3024; Falcon Plastics Los Angeles, Calif.) on Roswell Park Memorial Institute Medium 1640 (Grand Island Biological Company, Grand Island, N.Y.) containing 10% fetal calf serum and antibiotics (1000 units per ml. of penicillin; 1000 mcg. per ml. of streptomycin; 2.5 mcg. per ml. of Fungizone and 600 mcg/ml. of Tylocine). Stock cultures are refed two times per week and subcultured at one to two week intervals.

Tissue cultures of the content inhibited cell line (ATCC No. CRL-1479) are grown in RPMI 1640 medium containing 10% fetal calf serum and antibiotics until they achieve confluence. The growth medium is then replaced with serum free RPMI 1640 and the cells maintained for 48 hours in this medium. This medium is conditioned by the cell growth. After 48 hours, this medium (serum free conditioned medium) is centrifuged at 1500 rpm to remove detached cells and the supernatant is lyophilized directly and stored at minus 20° C.

One hundred and fifty ml of phenyl-sepharose (available as phenyl sepharose CL-4B from Pharmacia Fine Chemicals AB Piscataway, N.J.) is admixed with 500 ml of 10 mM Tris.HCl buffer containing 4M sodium chloride (pH 8.0) at room temperature. The buffered phenyl-sepharose mixture is poured through a 1.5 by 90 centimeter fractionation column (Pharmacia Model K15/90) until the entire contents of the beaker has been emptied and the column retains about 150 ml of packed phenyl-sepharose.

The lyophilate derived from 60 ml. of conditioned culture medium is dissolved in 100 ml. of the 10 mM tris.HCl, 4 M NaCl buffer, dialyzed against it (sausage casing membrane) for 48 hours and the dialysis fluid changed several times. The final dialysis is made against distilled water for 24 hours, with several changes of dialysis fluid. The dialyzed serum free conditioned medium is then lyophilized and stored at −20° C. until ready for use. Contact inhibitory factor is isolated from the pooled, dialyzed, lyophilized, 48-hour serum free conditioned medium.

The dialyzed, lyophilized serum free conditioned medium samples are re-dissolved in 10-20 ml of 4 M NaCl, 10 mM Tris. HCl (pH 8.0) buffer above and applied to the phenyl-sepharose column. The column is run at ambient (22°-27° C.) temperatures. The column eluate is monitored at 280 nm. The UV monitor is set to zero against the 4 M NaCl buffer. The original buffer is also used as the first elution buffer and is continuously flowed through the column until the initial 280 nanometer absorption peak returns to base line. UV absorbance is monitored at 280 nanometers with a conventional UV monitor (LKB, 2089-UVICORD III).

The portion of the serum free conditioned medium sample remaining bound to the column is sequentially eluted in stepwise fashion with a series of buffers of decreasing ionic strength at pH 8.0. The composition of these buffers is shown in the following table:

| Buffer No. | Tris HCl(millimolar) | NaCl(M) |
|---|---|---|
| 1 | 10 | 2 |
| 2 | 10 | 1 |
| 3 | 10 | 0.5 |
| 4 | 10 | 0.2 |
| 6 | 10 | 0.1 |
| 7 | 10 | 0 |

In each instance the buffer is flowed through the column at a rate of 1 ml per minute until the UV monitor recording indicates that the 280 nm peak has returned to the base line. When the base line is reached, the buffer is changed to the next lower ionic strength buffer in the series. The material eluting with these buffers is discarded. After the stepwise decreasing ionic strength buffers have been applied to the column and eluted, a final (eighth) elution is made using unbuffered distilled water. The loading and elution sequence takes between about 2–3 days. The entire 280 nM peak eluting with the unbuffered distilled water is pooled, dialyzed overnight against distilled water (two changes) and then lyophilized. The lyophilized material is stored at −20° C. for subsequent testing in tissue culture.

Table No. 1 (below) is a comparison of the molecular sieve method previously used to isolate contact inhibition factor and the hydrophobic interaction technique of the present invention.

The effectiveness of the 280 nM fraction eluted with unbuffered distilled water is assayed against malignant cell cultures to determine its efficacy in restoring contact inhibition (density dependent growth). Immediately prior to testing, each lyophilized sample is dissolved in 0.5-2.0 milliliters of distilled water and then two volumes of ethanol are added. The sample is kept overnight at −20° C. The ethanol precipitate is collected and used for all subsequent experiments as it has been found that the biologic (contact inhibitory) activity resides in the ethanol precipitate. The ethanol soluble substances in the supernate show no in vitro activity towards malignant (RPMI 1846) cells.

The efficacy of the ethanol precipitate is tested against tissue cultures of freshly plated cells of the RPMI No. 1846 line, growing in RPMI 1640 medium containing 10% fetal calf serum and antibiotics (as above).

The ethanol precipitate is dissolved in sterile phosphate buffered saline (0.1 molar phosphate, 0.5 molar NaCl pH 7.2-$KH_2PO_4$ 0.20 grams per liter; KCl 0.20 grams per liter; NaCl 8 grams per liter; $Na_2HOP_4 \cdot 7H_2O$, 2.16 grams per liter). The phosphate buffer solution is free of calcium and magnesium. The concentration of protein in this solution is determined by the Lowry method. Sufficient growth medium (RPMI 1640, 10% fetal calf serum and antibiotics) is added to adjust the final concentration as desired (Table II). Freshly trypsinized suspensions (above) of RPMI 1846 cells in culture media (above) are plated (10,000 cells per well) into multiple wells of Falcon Micro Test II plates. The fraction made from the ethanol precipitate (derived by eluting the column with unbuffered distilled water) was found to be highly active in restoring a contact inhibited state to the RPMI 1846 hamster amelanotic malignant melanoma cells. The cell densities and percent inhibition of growth of RPMI 1846 hamster melonoma cell cultures treated with varying concentrations of the highly purified contact inhibitory factor obtained according to the process of the present invention is illustrated in Table II.

TABLE II

CELL DENSITIES OF HAMSTER MELANOMA CELL CULTURES TREATED WITH HIGHLY PURIFIED CONTACT INHIBITORY FACTOR (CIF)

| CONC. OF PROTEIN IN CIF (mcg/ml) | Cells/Well | Viability (%) | % Inhibition of Growth |
|---|---|---|---|
| 0 (control) | $1.705 \times 10^5$ | 92 | — |
| 0.45 | $1.670 \times 10^5$ | 95 | 2.0 |
| 0.9 | $1.300 \times 10^5$ | 89 | 23.5 |
| 1.5 | $1.265 \times 10^5$ | 90 | 25.6 |
| 3 | $1.1325 \times 10^5$ | 85 | 33.4 |
| 6 | $0.9525 \times 10^5$ | 91 | 44.1 |
| 12 | $0.6050 \times 10^5$ | 89 | 64.5 |
| 25 | $0.0900 \times 10^5$ | 0 | 100 |

Referring to Table II it will be seen that inhibition of growth was obtained with CIF concentrations as low as 0.45 micrograms per milliliter, while significant inhibition was obtained at 0.9 micrograms per milliliter of CIF. The high level of activity at relatively low concentration indicates the relative purity of the contact inhibitory factor isolated by hydrophobic affinity separation.

Addition of RPMI 1640 media (supplemented with calf serum and antibiotics) containing CIF obtained according to the method of the present invention to subconfluent cultures of malignant RPMI 1846 melanocytes yields, on confluence, the contact inhibited state. The morphology of the RPMI 1846 malignant melanoma cell cultures grown on the test media (containing CIF obtained according) to the process of the present invention in varying concentrations) changes from a multi-layered overgrowth of disoriented, pleomorphic, easily detached cells to monolayers of well oriented, fibroblast-like, cohesive, and substrate adherent cells. Both morphological and growth inhibitory effects of the contact inhibitory factor have been shown to transcend species barriers, extending equally to malignant melanocytes of man and mouse. It has been found that the contact inhibitory factor isolated according to the invention effectively inhibits the growth of a variety of cell types, both malignant and non-malignant, of ectodermal, mesodermal, and endodermal origins. The growth inhibition is concentration-dependent, reversible, and non-toxic at moderate concentration, but is increasingly lethal at high concentrations (greater than 25 micrograms per liter). In cultures of RPMI 1846 cells plated on Roswell Park Memorial Institute Medium 1640 supplemented with 10% fetal calf serum and antibiotics, the addition of 6 micrograms per milliliter of CIF to the test medium yielded a decrease in saturation density on the order of 44%.

In addition to the growth inhibitory effects, consistent morphological changes were also observed in those cell cultures grown on media containing the contact inhibitory factor. These cultures were less crowded, and cells were enlarged, remaining in adherent monolayers rather than piling up or detaching. Although the CIF treated cultures show decrease of greater than 50% in saturation density, there is no loss of viability. It has also been found that the growth inhibitory effect is reversible. Replacement of CIF containing medium with CIF free medium was followed, within less than 24 hours, by reversion of cells to the dendritic shape and by the appearance of the disoriented, multi-layered morphology, as cells resumed further growth. However, such disoriented cultures again responded to the latter readdition of "factor", although this required, in heavily overgrown cultures, up to a week or more. Cell viability of contact inhibited cultures, as judged by exclusion of Trypan Blue was the same as in controls, 91%. The biological effectiveness of the CIF produced according to the present invention was preserved in complete culture medium at 4° C. for 2 weeks.

While not wishing to be bound by any particular theory, it is believed that CIF may be a protein and/or polysaccharide in view of its UV absorption at 280 nM and staining characteristics on polyacrylamide gels. While the mechanism of action of CIF has not been specifically identified, it may inhibit the expression of abnormal properties by the cells' genes. CIF is not dialysable but can be precipitated in ethanol. It may therefore be a protein or polysaccharide having a relatively high molecular weight. In vitro tests have shown that CIF is operative across species barriers as well as tumor barriers. CIF has reduced cell growth in cultures of malignant melanomes (hamster, mouse and human) and in colon carcinoma cells (human), rhabdomyosarcoma cells (human), and neuroblastoma cells (mouse).

The addition of CIF to subconfluent cultures also resulted in substantial reductions in saturation densities of all cell types tested, both transformed and contact inhibited cell types, without loss of viability (as judged by dye exclusion tests) when compared to controls omitting the CIF. In general the CIF treated cultures were less crowded and cells were enlarged, remaining in adherent monolayers.

To further evaluate the active material produced according to the present invention concentrated CIF material obtained by molecular sieving (Sephadex G-200-Table I) and the ethanol precipitate of the present invention (containing CIF) were subjected to electrophoresis on polyacrylamide gels. In each instance, the concentrated material was made up with 1% sodium dodecylsulfate, 1 mM 2-mercaptoethanol, and 60% sucrose; 40–60 micrograms per 40–60 microliters were layered on the gels which were 9 centimeters in length and 0.4 centimeters in diameter. The amount of the active material was estimated by the Lowry method using bovine serum albumin as a standard. The final gel composition was 5% acrylamide (recrystallized), 0.12% N, N'-bis-methylene acrylamide, 0.1% Na dodecyl sulfate, 0.1 M sodium phosphate buffer, pH 7.1, 0.05% N, N, N',N'-tetramethylenediamine, and 0.075% ammonium persulfate. The electrode buffer was 0.1 M sodium phosphate, pH 7.1 containing 0.1% Na dodecyl sulfate. Electrophoresis was carried out at 10 ma per gel for 4 hours. The gels were stained for 60 minutes in 0.25% Coomassie brilliant blue in water-methanol-acetic acid 5:5:1, and destained in water-methanol-acetic acid 17:1:2 until clarified. Inspection of the SDS-polyacrylamide gel of the ethanol precipitate of peak eight (phenyl-sepharose fractionation) revealed a single, relatively narrow stained band. In contrast, the gel of the active "factor" obtained by sephadex fractionation contained three bands located at widely spaced apart positions on the gel. (Reference Lipkin et al Proceedings of the National Academy of Science, ibid). The lowest band on this gel was relatively broad as compared with the width of the single band obtained from electrophoresis of the phenyl-sepharose gel. The presence of a single band on the phenyl-sepharose gel (containing the unbuffered distilled water eluate at 280 nM) indicates that this fraction is relatively pure and probably comprises a single protein. In contrast, the presence of three bands, one of which is extremely broad, on the gel obtained by electrophoresis of the sephadex fraction indicates that this material is relatively crude and comprises many proteins of widely varying molecular weights and compositions.

The composition of RPMI 1640 is shown in the following table III:

TABLE III

| COMPONENT | RPMI 1640 (mg/L) |
|---|---|
| INORGANIC SALTS | |
| $CaCl_2$ | 100.00 |
| $Ca(NO_3)_2 \cdot 4H_2O$ | 400.00 |
| KCl | 48.84 |
| $MgSO_4 \cdot 7H_2O$ | 100.00 |
| NaCl | 6000.00 |
| $NaHCO_3$ | 2000.00 |
| $Na_2HPO_4 \cdot 7H_2O$ | 1512.00 |
| OTHER COMPONENTS | |
| Glucose | 2000.00 |
| Glutathione (reduced) | 1.00 |
| Phenol red | 5.00 |
| AMINO ACIDS | |
| L-Arginine (free base) | 200.00 |
| L-Asparagine | 50.00 |
| L-Aspartic acid | 20.00 |
| L-Cystine | 50.00 |
| L-Glutamic acid | 20.00 |
| L-Glutamine | 300.00 |
| Glycine | 10.00 |

TABLE III-continued

| COMPONENT | RPMI 1640 (mg/L) |
|---|---|
| L-Histidine (free base) | 15.00 |
| L-Hydroxyproline | 20.00 |
| L-Isoleucine (Allo free) | 50.00 |
| L-Leucine (Methionine free) | 50.00 |
| L-Lysine HCl | 40.00 |
| L-Methionine | 15.00 |
| L-Phenylalanine | 15.00 |
| L-Proline(Hydroxy L-Proline free) | 20.00 |
| L-Serine | 30.00 |
| L-Threonine (Allo free) | 20.00 |
| L-Tryptophan | 5.00 |
| L-Tryosine | 20.00 |
| L-Valine | 20.00 |
| VITAMINS | |
| Biotin | 0.20 |
| D-Ca pantothenate | 0.25 |
| Choline Cl | 3.00 |

Based on the existing evidence, it appears that the molecular weight of the active CIF principle is >10,000D. The supporting evidence includes the fact that the active principle is non-dialyzable using membranes which do not pass molecules of molecular weight greater than 10,000D; the active principle is precipitated with ethanol, a property usually associated with molecules of molecular weight >10,000.

It has also been determined that the active CIF principle is moderately hydrophobic and water soluble. The moderate hydrophobicity is indicated by its failure to elute from the hydrophobic affinity column with ionic buffers (even very weakly ionic buffers, e.g. 10 mM Tris.HCl).

In view of the procedure used to isolate the active CIF, it is clear that CIF is stable and soluble in distilled water and in buffers of up to 4 M NaCl. The CIF material of the present invention retains its biologic activity, even after being stored at 4° C. for periods in excess of one week.

The FIGURE illustrates the elution profile of the ATCC No. CRL-1479 serum free conditioned medium from phenyl-sepharose. Elution profile of serum free conditioned ATCC No. CRL-1479 medium from phenyl-sepharose.

TABLE I

| Source | Original 48 hr. serum free conditioned medium (ATCC No. CRL-1479) | Improved 48 hr. serum free conditioned medium (ATCC No. CRL-1479) |
|---|---|---|
| Processing: (a) Preparation prior to application to column | | |
| 1 First buffer for solution | 0.15 M NaCl | 10 mM Tris 4 M NaCl pH 8.0 |
| 2 First dialysis | 0.15 M NaCl | same as above |
| 3 Second dialysis | 0.15 M NaCl | distilled water |
| 4 Concentration method | evaporation under vacuum at room temperature | lyophilization |
| 5 Storage | (No storage possible; must go directly onto column) | −20° C. |
| (b) Column technique | | |
| | (cold room 4° C.) | (22–27° C.) |
| 1 Packing material | Sephadex G-200 | Phenyl-sepharose |
| 2 Equilibration buffer for column | 0.1 M Tris . HCl 1 M NaCl pH 8.0 | 10 mM Tris . HCl 4 M NaCl pH 8.0 |
| 3 Elution buffer | 0.15 M NaCl | Tris (mM) NaCl (M) a 10 2 |

TABLE I-continued

| Source | Original 48 hr. serum free conditioned medium (ATCC No. CRL-1479) | Improved 48 hr. serum free conditioned medium (ATCC No. CRL-1479) | |
|---|---|---|---|
| | | b | 10 | 1 |
| | | c | 10 | 0.5 |
| | | d | 10 | 0.2 |
| | | e | 10 | 0.1 |
| | | f | 10 | 0 |
| | | g | distilled H$_2$O | |
| 4 Theoretical basis for separation column | Molecular Sieving | Hydrophobic affinity | |
| (c) Post-column processing | | | |
| 1 Concentration | evaporation at room temperature | — | |
| 2 dialysis | 0.1 M phosphate buffer, pH 7.1 | distilled H$_2$O | |
| 3 Concentration | — | lyophilization | |
| 4 storage | — | −20° C. | |
| (d) preparation of sample for bio-assay | | | |
| | Precipitated with 2 volumes of ethanol from a solution of 0.1 M phosphate at pH 7.1. The sample is kept at −20° C. overnight | The lyophilized sample is dissolved in distilled H$_2$O and then two volumes of ethanol added. The sample is kept overnight at −20° C. | |

What is claimed is:

1. A method for the isolation of a biologically active factor that restores contact inhibition of growth to malignant cell types which comprises
applying a sample comprising media conditioned by growth of a contact inhibited cell culture to a fractionating column comprising a non-ionic hydrophobic affinity material, the hydrophobic binding interaction of said material with proteins capable of being modified in the presence of buffers of varying ionic strength,
sequentially eluting the column with buffers of decreasing ionic strength,
applying unbuffered distilled water to said column as the final eluting medium,
collecting the unbuffered distilled water eluate from said column,
lyophilizing the eluate to a powder,
dissolving the powder in distilled water to form a solution, and
adding ethanol to the solution to form a precipitate comprising said factor, said factor having a UV peak absorbance at about 280 mm being non-dialyzable, hydrophobic and water soluble.

2. The method of claim 1 wherein said hydrophobic affinity material comprises phenyl-sepharose.

3. The method of claim 2 which comprises monitoring the ultraviolet absorption spectra of the distilled water eluate from the column at 280 nM.

4. The method of claim 3 wherein said buffers of decreasing ionic strength comprise solutions of 10 mM Tris HCl containing 2 molar NaCl, 1 molar NaCl, 0.5 molar NaCl, 0.2 molar NaCl, 0.1 molar NaCl and 0 molar NaCl.

5. The method of claim 3 which comprises dialyzing the unbuffered distilled water eluate against distilled water.

6. The method of claim 5 which comprises lyophilizing the unbuffered distilled water eluate to a powder.

7. The method of claim 6 which comprises redissolving said powder in distilled water.

8. The method of claim 7 which comprises precipitating the redissolved lyophilized powder with ethanol and collecting the solid precipitate.

9. The method of claim 8 wherein said media comprises serum free conditioned media.

10. The method of claim 9 wherein said serum free conditioned media is obtained from 48 to 72 hour old cultures of contact inhibited cells maintained in the absence of serum.

11. The method of claim 10 wherein said cells are a culture of ATCC No. CRL-1479 cells.

12. The method of claim 10 wherein said sequential elution is conducted at a temperature of between about 22° and 27° C.

13. The method of claim 12 wherein said sequential elution is conducted at 25° C.

14. The method of claim 13 wherein said sequential elution comprises application of seven buffer solutions of decreasing ionic strength to said column.

15. The method of claim 14 which comprises lyophilizing said serum free conditioned media, dissolving said media in a buffer comprising 10 mM Tris.HCl, 4 M NaCl at pH 8.0,
dialyzing said solution at 4° C. against said buffer, lyophilizing the dialyzed conditioned media again to form a powder and redissolving the powder in said buffer.

16. The method of claim 15 which comprises washing said phenyl-sepharose column with distilled water and with said 10 mM Tris.HCl, 4 M NaCl at pH 8.0 buffer prior to applying serum free conditioned media to said column.

17. The method of claim 16 wherein said phenyl-sepharose is prepared by cross-linking agarose with 2,3-dibromopropanol, desulphating the resulting gel by alkaline hydrolosis under reducing conditions to form a gel matrix, and reacting said matrix with a glycidyl ether.

18. The method of claim 16 which comprises monitoring the UV wavelength of the eluate from said column at 280 nM.

19. A composition comprising a contact inhibition factor that restores contact inhibition of growth to malignant mamalian cell types, said composition being prepared by applying a sample comprising media conditioned by growth of a contact inhibited cell culture to a fractionating column comprising a non-ionic hydrophobic affinity material, the hydrophobic bonding interaction of said material with proteins capable of being modified in the presence of buffers of varying ionic strength,
sequentially eluting the column with buffers of decreasing ionic strength,
applying unbuffered distilled water to said column after eluting with said buffers of decreasing ionic strength,
collecting the material eluting with the distilled water,
lyophilizing the distilled water to said column after eluting with said buffers of decreasing ionic strength,
collecting the material eluting with the distilled water,
lyophilizing the distilled water eluant to a powder,
dissolving the lyophilized powder in distilled water to form a solution, adding ethanol to said solution to form a precipitate comprising said factor, and collecting said solid precipitate, said factor having a positive reaction in the Lowery assay for protein, being active to restore contact inhibition of growth in cultures of non-contact inhibited cells a UV peak absorbance at about 280 nm, being non-dialyzable, hydrophobic and water soluble and having a molecular weight in excess of 10,000 Daltons.

20. The method of restoring contact inhibition of growth to malignant cell types which comprises administering an effective dose for restoring contact inhibition of the composition of claim 19 to said malignant cell types.

* * * * *